United States Patent [19]
Jindra

[11] Patent Number: 5,233,517
[45] Date of Patent: Aug. 3, 1993

[54] EARLY GLAUCOMA DETECTION BY FOURIER TRANSFORM ANALYSIS OF DIGITIZED EYE FUNDUS IMAGES

[76] Inventor: Lawrence F. Jindra, 92 Cisney Ave., Floral Park, N.Y. 11001

[21] Appl. No.: 516,480

[22] Filed: Apr. 30, 1990

[51] Int. Cl.$^5$ .................... G06F 15/00; A61B 6/00; A61B 13/00; G01J 1/42
[52] U.S. Cl. ...................... 364/413.13; 128/654; 128/745; 356/223
[58] Field of Search .............. 364/413.13, 413.03, 364/487, 572; 395/118; 382/6; 358/98, 160; 351/221; 128/745, 648

[56] References Cited

U.S. PATENT DOCUMENTS

| | | | |
|---|---|---|---|
| 4,249,825 | 2/1981 | Shapiro | 128/654 |
| 4,743,107 | 5/1988 | Aizu et al. | 351/221 |
| 4,950,070 | 8/1990 | Aizu et al. | 351/221 |
| 4,991,584 | 2/1991 | Kobayashi et al. | 128/648 |
| 5,016,173 | 5/1991 | Kenet et al. | 364/413.13 |

Primary Examiner—Donald E. McElheny, Jr.
Assistant Examiner—Khai Tran
Attorney, Agent, or Firm—Siegmar Silber

[57] ABSTRACT

Early glaucoma detection by a system and a method of fast Fourier transform analysis of digitized eye fundus images is disclosed. In this system, a red-free photograph of the eye fundus is first converted to digital form, and then the topography is further studied by taking sectional views, each of which is restated as a waveform. Each waveform represents the outline of the hills and valleys or "landscape" of the eye fundus and has a low signal-to-noise ratio. The noise is filtered out by taking adjacent slices and averaging the waveform signals thereof. Optionally, linear regression and window functions are used to eliminate trend and endpoint effects. This reduced digitized data is now the RNFL image in spatial frequency components. Using a fast Fourier transform function to calculate the power spectrum at each spatial frequency, the waveform is graphically represented on a printer/plotter. When resultant waveforms representative of RNFL topographic sections are presented from spaced-in-time eye fundus photographs, comparisons thereof are usable to provide early diagnoses and to monitor the progress of pathological conditions, especially glaucomatous conditions. In glaucoma throughout the progress of the disease, the landscape continually flattens, and, thus, this method of digitized imaging is useful in detecting previously indiscernible changes.

20 Claims, 3 Drawing Sheets

EARLY GLAUCOMA DETECTION BY FOURIER TRANSFORM ANALYSIS OF DIGITIZED EYE FUNDUS IMAGES

BACKGROUND OF THE INVENTION

1. Field of the Invention

This invention relates to a method of computer aided interpretation of retinal nerve fiber layer images, and more particularly to a method of mathematically analyzing such images after the images have been expressed in digital form.

2. Information Disclosure Statement

Over the immediate past few decades, some further understanding of glaucoma and related diseases has been gained. Ophthalmic medicine broadly equates retinal nerve fiber layer (RNFL) deterioration and degeneration to optic neuropathological conditions, especially glaucoma, and uses as diagnostic tools visual examination, intraocular pressure (IOP) measurements, eye fundus photography, manual and computerized visual field results, and ocular angiogram analysis. While not all of these tests are indicated for every patient, advances in technology have enhanced each of the previously named areas. As the disclosure which follows concerns ophthalmography and more specifically, eye fundus photography, the balance of this discussion is limited thereto. The Applicant is familiar with eye fundus camera literature in Class 351, Subclasses 006.000, 007.000, 013.000, 014.000, and 016.000 and is unaware of any applicable references contained therein. A pre-examination medical literature search was conducted and uncovered the following:

Caprioli; Joseph; et al. "Videographic Measurements of Optic Nerve Topography in Glaucoma," *Investigative Opthalmology & Visual Science*, Vol. 29, No. 8 (August, 1988) pp. 1294–1298.

Cooper, Richard L.; et al. "Computerized Densitometry of Red-Free Retinal Photographs Correlated with Automatic Perimetry," *Current Eye Research*, Vol. 7, No. 8 (1988) pp. 789–799.

Lundstrom, Mats, et al. "Computer Densitometry of Retinal Nerve Fibre Atrophy," *Acta Ophthamologica*, Vol. 58 (1980), pp. 639–644.

Mitra, Sunanda; et al. "Automated method for Fundus Image Registration and Analysis," *Applied Optics*, Vol. 27, No. 6 (Mar. 15, 1988), pp. 1107–1112.

Peli, Eli; et al. "Computerized Enhancement of Retinal Nerve Fiber Layer," *Acta Ophthamologica*, Vol. 64 (1986), pp. 113–122.

Caprioli et al. have used computerized digital analysis techniques of the optic nerve head to provide quantitative measurements of the optic nerve head topography. Cooper et al. have correlated retinal photographic density with field loss using histogram equalization. Mitra et al. have used spectrum analysis and cepstrum analysis to correct for rotational and translational shifts in image registration. Lundstrom et al have used computerized densitometry measurements to assess local density variation. Peli et al. have used digital analysis techniques, including contrast enhancement (histograph modification and extremum sharpening) for wedge defects; directional enhancement for slit defects; and, homomorphic filtering and adaptive enhancement for diffuse defects.

In the medical literature, there has been a widespread indication that early changes in retinal nerve fiber layer structure occur before measurable abnormalities are detected. While glaucoma is not fully understood, the structure of the RNFL has been studied extensively and it is known that, upon deterioration and degeneration of the RNFL, concomitant changes in optic nerve topography occur. Present ophthalmoscopic and ophthalmographic techniques do not yield sufficient topographic data.

DISCLOSURE OF THE INVENTION

The invention discloses a system and a method of image enhances ophthalmography (IEO). In the system of the applicant, a red-free photograph of the eye fundus is first obtained. The photograph is presented in a monochromatic transparency to a video camera. The presentation includes the use of a light box so as to provide diffused backlighting to the transparencies or the 35 mm slide. The video camera is associated with an image analyzer that has a central processing unit and a cathode ray tube display. From the video camera the video analog output signal is provided and is converted to digital form using an analog-to-digital converter. The acquisition of digital data is controlled by the "frame grabbing" portion of the image analyzing subsystem. The image analyzer also arrays the digital data so as to correspond with a 512×512 pixel array and facilitates the display thereof on the CRT monitor. To enable topographic studies of the eye fundus densitometric values are assigned to each bit of digital data at each pixel location. The topography is further studied by taking sectional views along selected lines determined by the ophthalmologist. The sectional view is stated as a waveform, which represents the outline of the hills and valleys of the eye fundus. Initially, because of the inherent nature of the data, the waveform presented has a low signal-to-noise ratio. The noise is filtered out of waveform by taking adjacent slices and averaging the waveform signals thereof. Additional filtering by signal processing is optionally performed by using linear regression and window functions to eliminate trend and endpoint effects. This also reduces the digitized data so that now the RNFL is presented in spatial frequency components. This data is now mathematically processed using mathematical software providing a fast Fourier transform function, which function calculates the power spectrum at each spatial frequency. After signal and mathematical processing, the waveform is graphically represented on a printer/plotter. When resultant waveforms representative of RNFL topographic sections are presented from spaced-in-time eye fundus photographs, the comparison thereof is usable to provide early diagnosis and to monitor the progress of pathological conditions.

Specifically, the pathophysiology of glaucoma indicates that during the disease deterioration and degeneration of the retinal nerve fiber layer occurs progressively. The RNFL forms a landscape of hills and valleys at the back of the eye which in a healthy eye is discernible through eye fundus photography. With a glaucomatous condition, the "landscape" begins to flatten and continues to do so throughout the progress of the disease. In visual inspections of present eye fundus photographs, small topographic changes are not visible. One of the objects of the present invention is to detect previously indiscernible changes through the application of digitized imaging, and, within such art, to provide by signal and mathematical processing of the data to accomplish this end. Other objects and features of the

DESCRIPTION OF THE PREFERRED EMBODIMENTS

Figure 1:
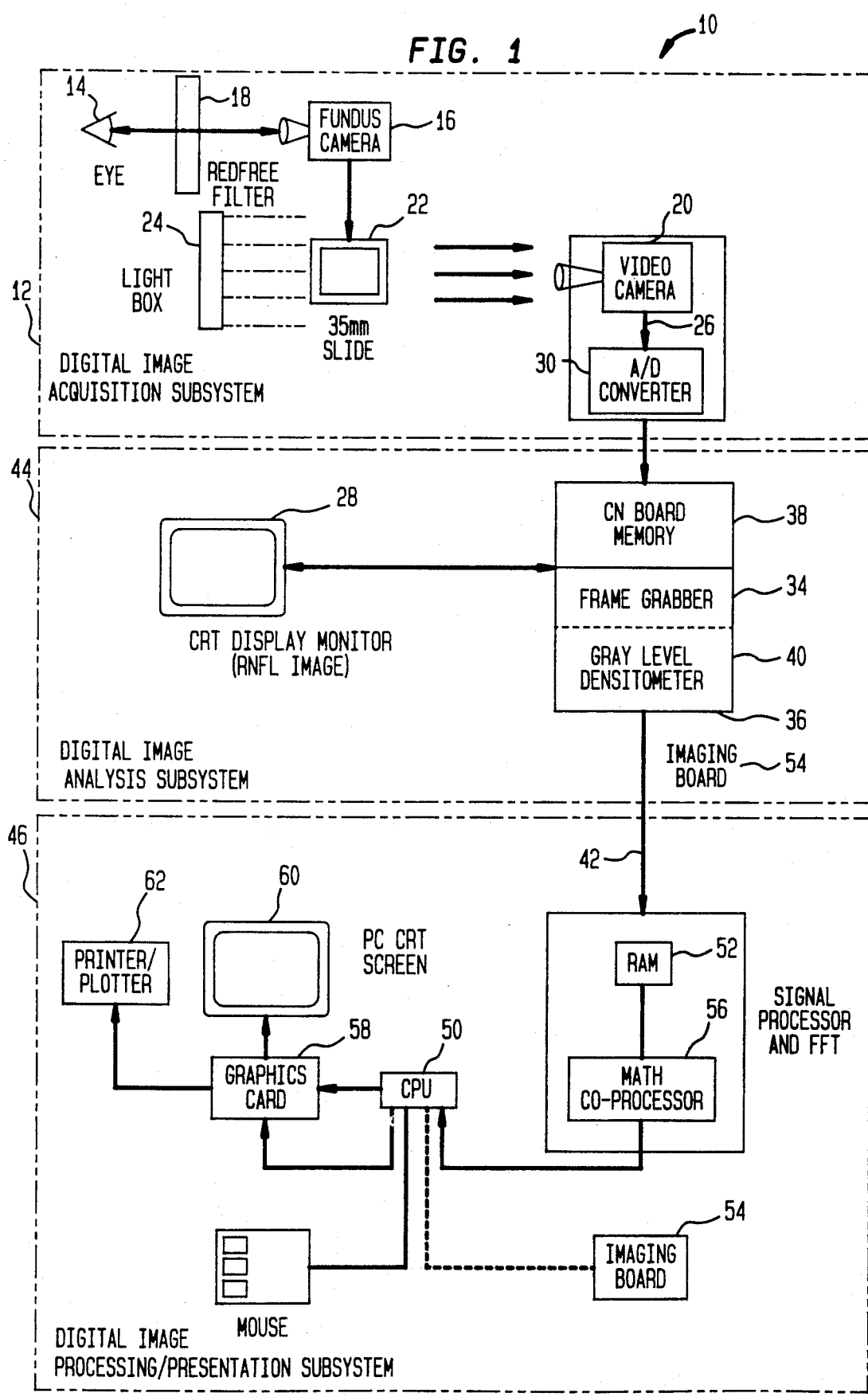
FIG. 1 is a schematic block diagram of the system of this invention.

In accordance with the invention, a red-free fundus image presented and a frame thereof is acquired in digital form by the Jindra Analyzer System (JAS). In the best mode of practicing the invention, the JAS is next used to define the profile of the RNFL or the topographic study being made. The digital image is then analyzed by first performing gray-level densitometry along the length of the profile and forming an initial waveform which is reflective of the spacing of the nerve fibers of the RNFL and the frequency thereof. The waveform is processed by the JAS to reduce noise inherent in the initial acquisition and to eliminate trend and endpoint effects. The processed or modified waveform undergoes fast Fourier transform analysis, which analysis calculates the Fourier power spectrum at each spatial frequency calibration (cy/mm). Finally, a graphic representation of the power spectrum is generated. The graphic display is used to provide an early diagnosis of a glaucomatous condition by detecting smaller incremental changes than what is observable by present ophthalmoscopy. A detailed description of the system and the methods of this invention are next presented.

The system of opthalmography and the method of use thereof of this invention arises from investigations using perimetry, contrast sensitivity evaluation, and other psychophysical techniques. The application of these techniques have indicated that significant damage to the optic nerve during a pre-glaucomatous condition well before conventionally defined and measurable defects of glaucoma are detected. Thus in most cases, the pre-glaucomatous condition or glaucoma is not being diagnosed at the earliest possible stage. By this invention, a new method of examining the retinal nerve fiber layer (RNFL) is disclosed that allows detection of early changes in RNFL structure. The system permits earlier diagnosis of injury to the optic nerve because of a pre-glaucomatous condition or glaucoma.

Conventional examination of the nerve fiber layer follows the guidelines described by Sommer et al. (Ref. *Arch. Ophthamol.*, 1982; 100:135-146.) Traditionally, the fundus has been examined with red-free ophthalmoscopy to evaluate progressive changes occurring in the structure and appearance of the diseased RNFL. These begin with the appearance of slitlike defects, which progress to broader, wedge-like areas with loss of circumpapillary streaming. With diffuse loss, the retinal vessels stand out in stark relief against the attenuated RNFL.

The RNFL is composed largely of axons from the retinal ganglion cells (RGC). These fibers constitute the neural link between the eye and the brain. When viewed, as usual, in a plane perpendicular to the retina, the appearance of these fibers can enable the estimation of the structural integrity of the RNFL.

When these fibers are viewed from a plane parallel to the retina, the RNFL, from this perspective, forms a contour surface of hills and valleys. As the contour surface changes are more reflective of incremental changes, the system and method of this invention use such changes to more accurately quantitate the RNFL dynamics. This occurs by noting the shift in relative spatial frequency contribution to the power spectrum and comparing the same with a power spectrum analysis of normal subject eye fundus photographs.

METHODS OF THE INVENTION

An indirect method can be used to measure variations in the contour surface. A red-free fundus slide is converted into a digital image using a commercially available imaging program. Densitometry measurements made from the resulting gray level data contained in the slide yield a digitized contour surface representing the densitometric evaluation of the RNFL. In this manner, the three-dimensional contour surface of the RNFL is converted into a 512×512 array containing numbers from 0 to 255.

A slice cut through this surface produces a two-dimensional waveform representing the topography of the RNFL. Conceptually similar to the profile view of the visual field obtainable using sophisticated perimeters, this complex waveform appears in a form similar to that of an EEG tracing. It is quite irregular and seldom in itself yields much information to the observer, although one study detailing densitometric measurement of this profile did report a gross change in the complexity of this wave-form (RNFL) directly correlated to the degree of optic nerve injury (Ref. Lundstrom et al, supra.)

It is clear that an evaluation of a patient with glaucoma requires a more sophisticated method of analyzing the waveform representing the topography of the RNFL. This is available by Fourier analysis which provides information about waveforms that is not obvious by visual inspection or by densitometric techniques. Through such analysis, a complex wave is decomposed into its simpler, constituent parts, and the relative contributions of these simple waves are quantitatively represented by a power spectrum. Without such analysis, when the waveform is first observed, the RNFL appears within normal limits or appears as a poorly defined collection of hills and valleys. However, the mathematical representation of the information contained in the profile line of the RNFL given by the fast Fourier transform reveals changes not detectable by other means. Thus, now with the present invention, even, when the fundamental component appears normal, defects are found in the harmonic components of the waveform.

In a normal retina, the nerve fiber-layer is tightly spaced. The individual fibers measure on the order of approximately 1 u; the bundles measure 90 to 240 us. This tight arrangement of the nerve fiber bundles means that, upon application of fast Fourier transforms, the power spectrum representation is concentrated at higher spatial frequencies. That is, because the fiber bundles are tighter, more of them fit into the same space on the retina. Hence, the nerve fibers are present at a higher spatial frequency. In a glaucomatous retina, with nerve fiber degeneration, the nerve fiber bundles thus become thinner and the constituent nerve fiber bundles of such a topography reflect looser "bundling" and lower contrast. In this case, the representative power spectrum does not show any significant amplitude at the higher spatial frequencies, especially as the looser bundling (or less regular arrangement) of the nerve fiber bundles shifts the power spectrum to lower spatial frequencies.

The use of fast Fourier transforms to analyze the RNFL has been validated with three cycles per millimeter in the Fourier power spectrum as an arbitrary cutoff to discriminate normal from glaucomatous RNFL. In such analysis, the Fourier power spectrum from normal RNFL shifts to higher spatial frequencies, and the power spectrum from glaucomatous RNFL shifts to lower ones.

Further, methods that include filtering, averaging, and Cepstrum analysis are viewed as enhancements of the results of the above technic. Combining these techniques of digital image analysis with video angiography allow for more comprehensive, real-time sampling.

IMAGE ENHANCED OPHTHALMOGRAPHY SYSTEM

Figure 2:
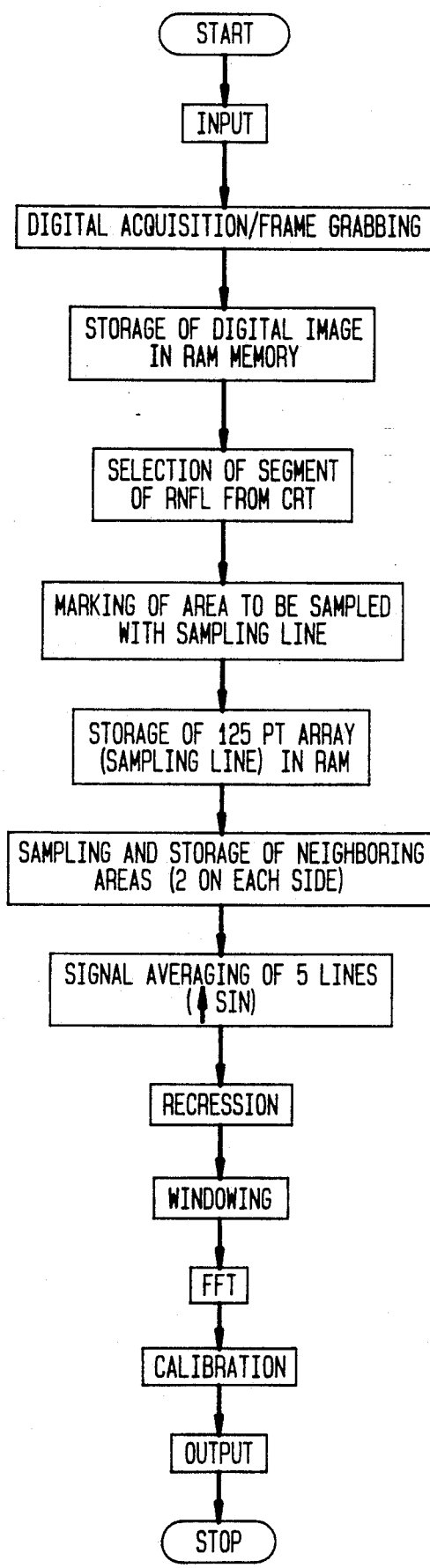
FIG. 2 is a simplified flow chart of the software for mathematical processing.
Figure 3:
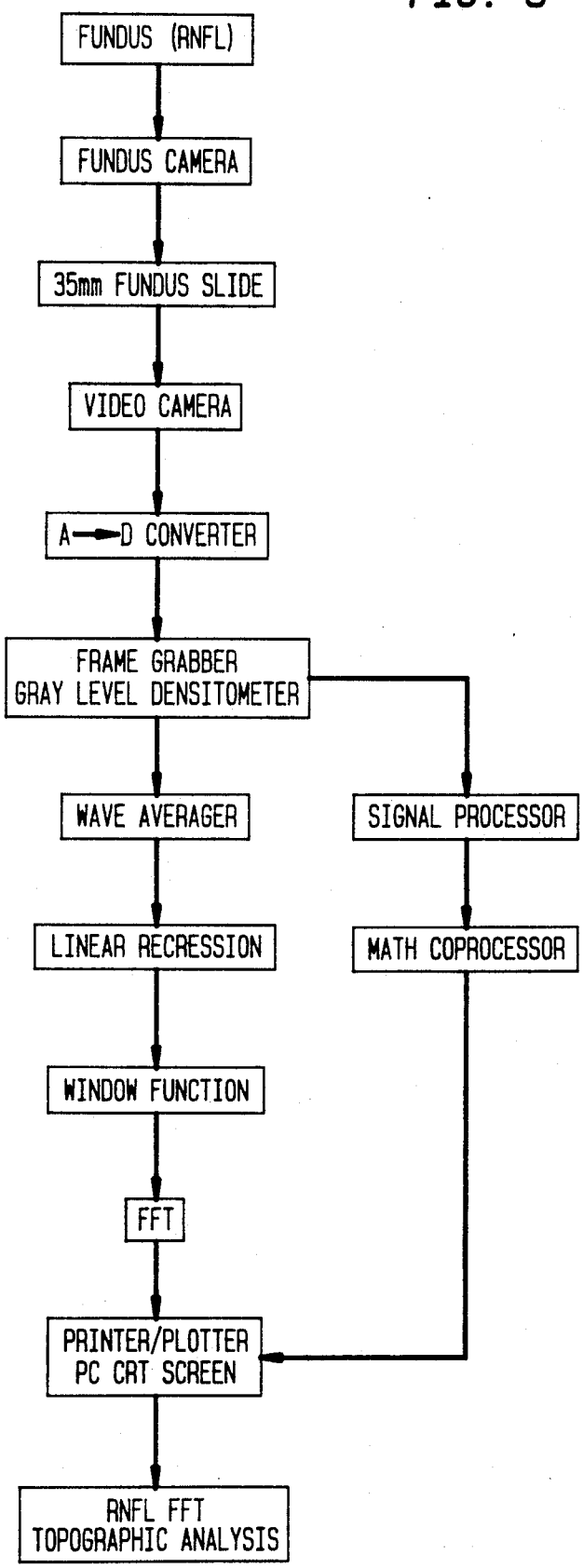
FIG. 3 is a simplified flow chart of the digital image analyzer portion of the system of FIG. 1.

Referring to FIGS. 1 through 3, the JAS system is next explained. In order to avoid inexactness in describing the blocks in the system diagrams and functions in the flow diagrams, certain terms are now defined.

Definitions

Regression Analysis: Removes the general trend of the wave, so that the endpoints are of equal value. Otherwise, the large general trend of the wave becomes the first major peak of the FFT power spectrum and obscures other findings. Regression analysis evaluates the slope of a line drawn through the wave and corrects the slope to zero (a flat line). In this way the cyclic character of the wave, and not the actual wave is examined.

Trend Effects: Trend effects are the resultant contribution to the FFT power spectrum that is introduced if the above regression analysis is not first performed. This contribution causes the trend of the wave to be included in the FFT power spectrum and obscures the cyclic character of the wave.

Window Function: The window function evaluates the point on a wave neighboring the examination site for large discontinuities, which discontinuities cause erroneous information to be included in the FFT power spectrum. This function acts to smooth localized disturbances in the local cyclic nature of the waveform.

Endpoint effects: Endpoint effects are the resultant disturbances in the FFT power spectrum if a window function is not used to remove sharp discontinuities in the data. These result in erroneous contributions to the FFT power spectrum.

Densitometric Values: The monochromatic image of the RNFL represented on the 35 mm fundus slide shows variety in light intensity as different shades of gray. The resultant differences in the density of this light intensity may be represented as densitometric values. Commonly these are represented as $2^8$ or 256 values from 0 to 255. These values may be stored as the value of light intensity of each picture element (pixel) making up an array, thereby digitizing the image.

Fourier Analysis: The French mathematician Joseph Fourier discovered that any complex cyclic wave may be decomposed into a sum of simpler cyclic waves. The resultant proportional contributions of each of these simpler waves determines the nature of the complex wave. These proportions may be determined by performing a Fast Fourier Transform (FFT) Analysis of the complex wave, to determine the resultant power spectrum, of the spatial frequency components of the simpler waves, making up this complex wave.

Description of the System

The image enhanced ophthalmography system is referred to generally by the reference numeral 10 and the digital image acquisition subsystem by the reference numeral 12. Initially, the ocular fundus 14 is photographed using a fundus camera 16 equipped with a red-free filter 18 for production of red-free images which accentuate the retinal nerve fiber layer (RNFL). A standard TV camera 20 is used to view a 35 mm slide 22 of the patient's fundus and RNFL, which slide is backlit by light box 24. An analog signal 26 is presented to a high-resolution CRT display monitor 28. This signal 26 is also is presented to an analog-to-digital converter 30 for processing to digitized form. A digitized image 42 is then acquired using a frame grabber 34 feature of a first imaging board 36. This digitized array of the fundus is stored in the on-board memory 38 of this imaging board 36. After processing by a gray-level densitometer 40, this digitized image 42 passes from the analysis subsystem 44 to the processing/presentation subsystem 46. There, the image 42 is utilized by the digital subsystem of the invention (PC CPU 50 and RAM 52, second imaging board 54, math co-processor 56, graphics card 58, and software subroutines) to perform the necessary averaging, filtering, FFT, and calibration, described in more detail hereinbelow, to yield the power spectrum of the spatial frequency components (in cycles/mm) of the RNFL. The resultant graph may be presented on the PC monitor CRT screen 60 or in hard copy form on a printer/plotter 62.

Explanation of Flow Chart of Digital Subsystem

An analog video signal representing the RNFL of the ocular fundus is presented to an analog-to-digital (A/D) converter. The resultant digital signal is stored as a 512×512 array in the on-board RAM of the imaging board. This signal is presented to a digital to analog converter, for reconversion into an analog signal, for presentation to the CRT display monitor as needed by the operator.

The digital signal also interacts with a frame grabber utility of the imaging program to digital acquire and store the digitized array of the fundus image. The ophthalmologist may then use an interactive mouse driven program to indicate the area of interest or segment for sampling purposes. This is usually a line of 125 points, representing a contour slice through the RNFL of the fundus image. Two parallel lines on either side of this selection line are then selected by the software subroutine. The five contour lines are then averaged to increase signal to noise ratio. The resultant averaged waveform is then filtered with a linear regression and window function to eliminate trend and endpoint effects, respectively. The resultant filtered waveform undergoes a Fast Fourier Transformation to yield the power spectrum of the spatial frequency components. These may be presented in calibrated form of cycles/mm, onto the PC CRT Screen or printer/plotter.

Explanation Of Flow Chart For Software

A digitized image of the RNFL that is viewed on the CRT display monitor is stored on the on-board RAM of the imaging board. The ophthalmologist views the CRT Display Monitor and selects an area of the RNFL, for examination. A line of 125 points, representing the densitometric values of the RNFL at these points, is then created and stored in the RAM of the PC. These gray scale values range between 0 and 255. The location of the line relative to the image is noted. Two parallel lines adjacent to either side of the sampling line are automatically selected and stored. The five lines are then signal averaged, to increase signal to noise ratio, to resultant in an averaged wave. A linear regression is performed on this wave to remove trend effects. A window function is then performed to remove endpoint effects. A Fast Fourier Transform is then performed to determine the spatial frequency power spectrum of the filtered wave. A calibration function is then performed to present the power function in cycles/mm. The resultant power spectrum may be displayed on the PC CRT screen or as hard copy from a printer/plotter.

In operating with the Jindra Analyzer System (JAS) of this invention a method is employed for the early detection of RNFL degeneration, which, in turn, indicates a diagnosis of glaucoma or a pre-glaucomatous condition. The method uses the system described hereinabove for image-enhanced ophthalmography for both detection and monitoring the RNFL. In the form of method steps, it is first described as one which employs the primary steps a. through g. set forth below. The method of this invention comprises the steps of:

a. acquiring a eye fundus monochromatic image in black and white form;
b. converting the monochromatic image into digital gray-level data representing densitometric values of the monochromatic image;
c. viewing the acquired image on a cathode-ray tube monitor;
d. selecting a segment of the acquired image for examination and enhancement;
e. arraying the densitometric values of the segment in an initial waveform;
f. enhancing the initial waveform by the substeps of:
    (1) applying signal processing techniques to provide a modified waveform; and,
    (2) mathematically processing the modified waveform by fast Fourier transform analysis; and,
g. comparing the processed, modified waveforms of two or more separate segments, each of said segments being the same segment of various views.

After completing these steps and upon comparison of the enhanced waveforms, optic neuropathological conditions are seen. Additionally, with the image-enhanced ophthalmography of this invention, a method of application is employed as described hereinabove; however, the image acquisition, of step a., further includes the following substeps:

(1) obtaining, through a red-free filter, an eye fundus photograph;
(2) viewing with a video camera the eye fundus photograph, the video camera having an analog output;
(3) defining a frame with predetermined area; and,
(4) converting, using an analog-to-digital converter, the analog output to digital data form.

Also, in the image acquisition, step a., for the photograph a 35 mm. transparency is utilizable and, for viewing, the transparency may be backlit with diffused light. Additionally, with the image-enhanced ophthalmography of this invention, a method of application is employed as described hereinabove; however, the waveform enhancement step, step f., may optionally include the signal processing steps of:

obtaining additional adjacent and parallel segments on either side of the selected segment of step d;
averaging the cross-section of the selected and additional segments; and,
substituting the averaged values for the values of initial waveform.

With this enhancement approach, the initial waveform may be modified to increase the signal-to-noise ratio and facilitate the analysis thereof. Also, the waveform enhancement step, step f., may include averaging two additional adjacent and parallel segments on either side of the selected segments with the five segments substantially equally spaced from respective adjacent segments. Further, the waveform enhancement step f., may include signal processing utilizing a window function and thereby eliminating endpoint effects in the fast Fourier transform analysis of the modified waveform. Yet further, the waveform enhancement step, step f., may include signal processing by utilizing linear regression technics and thereby minimizing trend effects in the fast Fourier transform analysis of the modified waveform.

The following steps summarize the processing described hereinabove:

presenting for comparison therewith power spectrum analyses of from spaced-in-time eye fundus photographs of the patient under examination; and,
noting the shift in the relative spatial frequency contribution to the power spectrum.

Although the present invention has been described with reference to particularly embodiment and examples, it will be apparent to those skilled in the art that variations and modifications can be substituted therefore without departing from principles and true spirit of the invention. The abstract given herewith is for the convenience of technical searches and is not for the interpretation of the scope of the invention.

What is claimed is:

1. A system of image-enhanced ophthalmography for detecting and monitoring a retinal nerve fiber layer, said system comprising:
    a. an eye fundus camera for providing a monochromatic photographic image in black and white form;
    b. conversion means for presenting said monochromatic image in digital gray-level data representing densitometric values;
    c. cathode-ray tube monitor means for viewing said monochromatic image, said cathode ray tube providing thereby an acquired image formed from said digital gray-level data;
    d. selection and display means for selecting a segment of the acquired image for further examination and enhancement, said selection and display means for arraying densitometric values of said segment in an initial waveform;
    e. enhancement program means for enhancing the initial waveform, said program means further comprising:
        (1) signal processing means for averaging and filtering the waveforms and thereby to provide a first modified waveform; and,
        (2) mathematically processing means for providing by fast Fourier transform analysis a second modified waveform; and,
    f. a comparator unit to differentiate said first and said second modified waveforms of two or more separate segments, each of said segments being the same segment of various views;

whereby, upon comparison of said enhanced waveforms, optic neuropathological conditions are provided.

2. A system as described in claim 1, wherein the eye fundus camera further comprises:
   (1) a red-free filter imposed upon said eye fundus camera;
   (2) video camera means for viewing said eye fundus photograph, said video camera having an analog output;
   (3) frame defining means for defining a frame area in cooperative functional relationship with said video camera, each said frame having a predetermined area; and,
   (4) analog-to-digital converter for converting said analog output of said video camera means to digital data form.

3. A system as described in claim 2, wherein the photographic image of said eye fundus camera is a 35 mm. transparency and, for viewing, said system includes a diffused light with which said photographic image is backlit.

4. A system as described in claim 1, wherein the enhancement program means further comprises a signal processor means for obtaining additional adjacent and parallel segments on either side of the selected segment and for averaging said parallel segments and deriving one or more averaged values; and, substituting the averaged values for the densitometric values of initial waveform;
   whereby the initial waveform is modified to have an increased signal-to-noise ratio and facilitate analysis thereof.

5. A system as described in claim 4, wherein the enhancement program means further comprises means for averaging two additional adjacent and parallel segments on either side of the selected segments with said segments substantially equally spaced from respective adjacent segments.

6. A system as described in claim 5 wherein the enhancement program means further comprises window function means for eliminating endpoint effects in the fast Fourier transform analysis of the modified waveform.

7. A system as described in claim 6 wherein the enhancement program means further comprises linear regression means for minimizing trend effects in the fast Fourier transform analysis of the modified waveform.

8. A method of image-enhanced ophthalmography for detecting and monitoring a retinal nerve fiber layer, said method comprising the steps of:
   a. acquiring an eye fundus monochromatic image in black and white form;
   b. converting the monochromatic image into digital gray-level data representing densitometric values of said monochromatic image;
   c. viewing the image acquired by step a. above, and converted by step b. above, on a cathode-ray tube monitor;
   d. selecting a segment of the acquired image for examination and enhancement;
   e. arraying the densitometric values of said segment in an initial waveform;
   f. enhancing the initial waveform by the substeps of:
     (1) applying signal processing techniques to provide a modified waveform; and,
     (2) mathematically processing the modified waveform by fast Fourier transform analysis; and,
   g. comparing the processed, modified waveforms of two or more separate segments, each of said segments being the same segment of various views;
   whereby, upon comparison of said enhanced waveforms, optic neuropathological conditions are provided.

9. A method as described in claim 8, wherein the image acquisition, step a., comprises the following substeps:
   (1) obtaining, through a red-free filter, an eye fundus photography;
   (2) viewing with a video camera said eye fundus photograph, said video camera having an analog output;
   (3) defining a frame with predetermined area; and,
   (4) converting, using an analog-to-digital converter, said analog output to digital data form.

10. A method as described in claim 9, wherein in the image acquisition, step a., said photograph is a 35 mm. transparency and, for viewing, said transparency is backlit with diffused light.

11. A method as described claim 8, wherein the waveform enhancement step, step f., further comprises the signal processing steps of:
    obtaining additional adjacent and parallel segments on either side of the selected segment of step d;
    averaging the cross-section of the selected and additional segments; and, substituting the averaged values for the values of initial waveform;
    whereby the initial waveform is modified to have an increased signal-to-noise ratio and facilitate analysis thereof.

12. A method as described in claim 11, wherein the waveform enhancement step, step f., further comprises averaging two additional adjacent and parallel segments, on either side of the selected segments with said segments substantially equally spaced from respective adjacent segments.

13. A method as described in claim 12 wherein the waveform enhancement step f., further comprises signal processing of utilizing a window function and thereby eliminating endpoint effects in the fast Fourier transform analysis of the modified waveform.

14. A method as described in claim 13 wherein the waveform enhancement step, step f., further comprises signal processing by utilizing linear regression techniques and thereby minimizing trend effects in the fast Fourier transform analysis of the modified waveform.

15. A method as described in claim 14 wherein the waveform enhancement step, step f., further comprises the substeps of:
    applying a calibration function means to a spatial frequency content of the fast Fourier transform analysis of the modified waveform; and,
    converting resultant data of the calibration into units of cycles/millimeter.

16. A method as described in claim 15 wherein the waveform enhancement step, step f., further comprises the substeps of:
    graphically displaying the resultant data of the calibration as the power spectrum of the spatial frequency components.

17. A method as described in claim 16 wherein the graphical display is presented on a computer monitor CRT screen.

18. A method as described in claim 16 wherein the graphical display is printed by a printer/plotter.

19. A method as described in claim 16 wherein the waveform enhancement step, step g., further comprises the substeps of:
- repeating the power spectrum presentation of the spatial frequency components for representative retinal nerve fiber layer topographic sections;
- presenting for comparison therewith power spectrum analyses of normal subject eye fundus photographs;
- noting the shift in the relative spatial frequency contribution to the power spectrum; and,
- thereby providing early diagnosis and monitoring of the progress of pathological conditions.

20. A method as described in claim 16 wherein the waveform enhancement step, step g., further comprises the substeps of:
- repeating the power spectrum presentation of the spatial frequency components for representative retinal nerve fiber layer topographic sections;
- presenting for comparison therewith power spectrum analyses of from spaced-in-time eye fundus photographs of the patient under examination;
- noting the shift in the relative spatial frequency contribution to the power spectrum; and,
- thereby providing early diagnosis and monitoring of the progress of pathological conditions.

* * * * *